United States Patent [19]

Horowitz

[11] Patent Number: 4,763,642

[45] Date of Patent: Aug. 16, 1988

[54] INTRACAVITATIONAL BRACHYTHERAPY

[76] Inventor: Bruce S. Horowitz, 33822 Yorkridge, Farmington Hills, Mich. 48018

[21] Appl. No.: 849,204

[22] Filed: Apr. 7, 1986

[51] Int. Cl.$^4$ .............................................. A61K 9/22
[52] U.S. Cl. .................................... 128/1.2; 604/891.1
[58] Field of Search .................. 128/1.1, 1.2; 604/890, 604/891

[56] References Cited

U.S. PATENT DOCUMENTS

| | | |
|---|---|---|
| 1,238,872 | 9/1917 | Bell . |
| 1,317,082 | 9/1919 | Hartenheim . |
| 1,494,826 | 5/1924 | Viol . |
| 1,517,861 | 12/1924 | Rosher . |
| 1,578,945 | 3/1986 | Withers . |
| 2,067,589 | 1/1937 | Antrim ........................................ 47/1 |
| 2,153,889 | 4/1939 | Hames .................................. 128/1.1 |
| 2,322,902 | 6/1943 | Wappler .................................. 29/34 |
| 2,517,513 | 8/1950 | Vaernet .................................. 128/272 |
| 2,829,636 | 4/1958 | Henschke .............................. 128/1.2 |
| 3,127,313 | 3/1964 | Glenn .................................... 167/51 |
| 3,351,049 | 11/1967 | Lawrence ............................ 128/1.2 |
| 3,463,158 | 8/1969 | Schmitt et al. ...................... 128/334 |
| 3,565,869 | 2/1971 | Prospero .............................. 260/78.3 |
| 3,589,356 | 6/1971 | Silverman ............................ 128/1.2 |
| 3,636,956 | 1/1972 | Schneider .......................... 128/335.5 |
| 3,663,685 | 5/1972 | Evans .................................... 424/1 |
| 3,750,653 | 8/1973 | Simon .................................. 128/1.2 |
| 3,867,190 | 2/1975 | Schmitt et al. .................... 117/138.8 |
| 3,872,856 | 3/1975 | Clayton ................................ 128/1.2 |
| 3,887,699 | 6/1975 | Yolles .................................. 424/14 |
| 3,927,325 | 12/1975 | Hungate, et al. .................... 250/435 |
| 3,948,263 | 4/1976 | Drake, Jr. et al. .................. 128/260 |
| 3,950,282 | 4/1976 | Gilbert et al. ........................ 260/9 |
| 3,976,071 | 8/1976 | Sadek .................................. 128/260 |
| 3,978,203 | 8/1976 | Wise .................................... 424/22 |
| 4,014,987 | 3/1977 | Heller et al. .......................... 424/15 |
| 4,052,988 | 11/1977 | Doddi et al. ...................... 128/335.5 |
| 4,054,138 | 10/1977 | Bucalo ................................ 128/260 |
| 4,086,914 | 5/1978 | Moore .................................. 128/1.2 |
| 4,096,239 | 6/1978 | Katz et al. ............................ 424/21 |
| 4,167,179 | 9/1979 | Kirsch .................................. 128/1.2 |
| 4,180,064 | 12/1979 | Heller et al. ........................ 128/130 |
| 4,182,750 | 1/1980 | Sullivan et al. ...................... 424/1 |
| 4,218,255 | 8/1980 | Bajpai et al. .......................... 106/45 |
| 4,249,531 | 2/1981 | Heller et al. ........................ 128/260 |
| 4,304,767 | 12/1981 | Heller et al. .......................... 424/78 |
| 4,309,776 | 1/1982 | Bergyer ............................ 604/891 X |
| 4,322,398 | 3/1982 | Reiner et al. ......................... 424/19 |
| 4,323,055 | 4/1982 | Kubiatowicz ........................ 128/1.2 |
| 4,351,337 | 9/1982 | Sidman ................................ 604/891 |
| 4,402,308 | 9/1983 | Scott .................................... 128/1.2 |
| 4,509,506 | 4/1985 | Windorski et al. .................. 128/1.2 |
| 4,510,924 | 4/1985 | Gray .................................... 128/1.2 |
| 4,534,760 | 8/1985 | Raible .............................. 604/891 X |
| 4,588,395 | 5/1986 | Lemelson ............................ 604/59 |

FOREIGN PATENT DOCUMENTS

| | | |
|---|---|---|
| 30822 | 6/1981 | European Pat. Off. . |
| 64860 | 11/1982 | European Pat. Off. . |
| 281869 | 10/1913 | Fed. Rep. of Germany ....... 128/1.2 |
| 297839 | 11/1929 | Fed. Rep. of Germany ....... 128/1.2 |
| 2240746 | 3/1975 | France . |
| 24693 | of 1906 | United Kingdom . |
| 704628 | 2/1954 | United Kingdom ................. 128/1.2 |

OTHER PUBLICATIONS

Vikram et al., "Non-Looping After Loading Technique for Interstitial Implants of the Base of the Tongue", Int. J. Radiation Oncology Biol. Phys., vol. 7, No. 3, pp. 419–422 (1981).

Martinez et al., "Sterilization of 125I Seeds Encased in Vicryl Sutures for Permanent Interstitial Implantation", Int. J. Radiation Oncology Biol. Phys., vol. 5, No. 3, pp. 411–413 (1979).

(List continued on next page.)

Primary Examiner—Edward M. Coven
Attorney, Agent, or Firm—Robert C. Kain, Jr.

[57] ABSTRACT

A delivery system for intracavitational brachytherapy comprising a body of material which is absorbable in animal tissue and a plurality of radioactive seeds within the body and encapsulated in the body. In one form, the body comprises a hollow exterior wall with a separate central chamber such that the hollow exterior wall will accommodate growth of body tissue such as brain tissue. In another form, the body comprises a solid hollow body having the seeds held in the center of the body that can be inserted in the cavity to be treated. In another form, a flat sheet is attached tangentially to the hollow exterior wall to facilitate placement over the brain.

10 Claims, 2 Drawing Sheets

OTHER PUBLICATIONS

Cunningham, The Physics of Radiology, 4th Ed., pp. 263–266 (1983).
3M Product Brochure I-125, Seeds in Carrier, Stamped Jul. 7, 1986.
"Radio Tags Bar Sponges in Patients", The Evening Star, p. A-20, Jul. 22, 1964.
M. Rotman et al., "Intracavitary Applicator in Relation to Complications of Pelvic Radiation", Int. J. Radiation Oncology Biol. Phys., vol. 4, pp. 951–956 (1978).
Blackshear, "Systems", Scientific American, pp. 66 et seq., Dec., 1979.

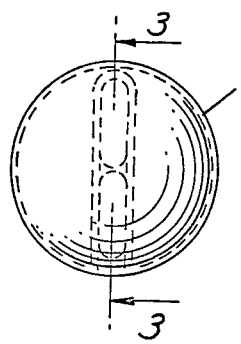
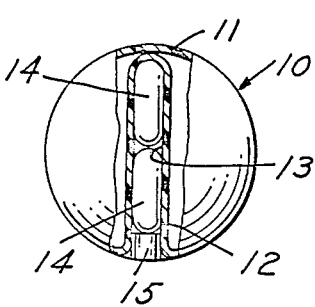
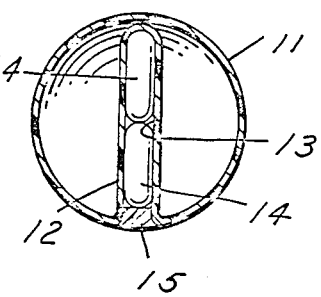
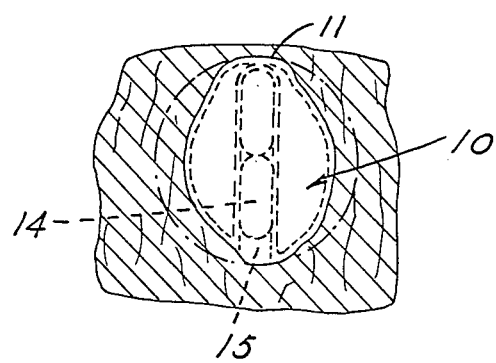
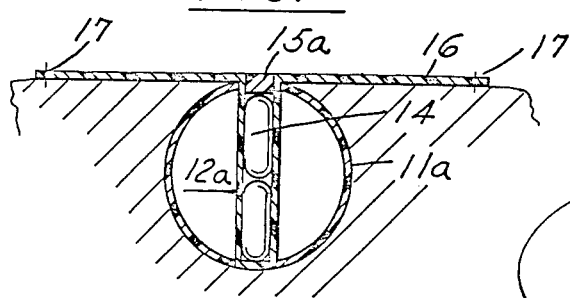
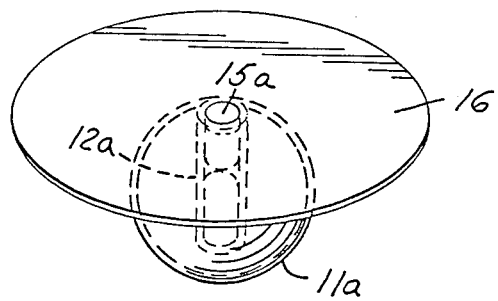

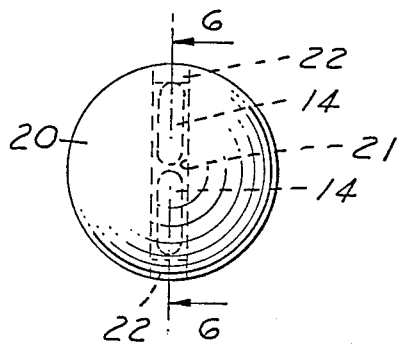
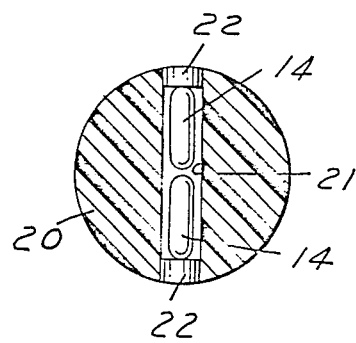
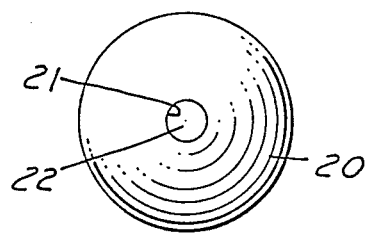

INTRACAVITATIONAL BRACHYTHERAPY

This invention relates to brachytherapy and particularly to intracavitational radiation therapy and a delivery system for intracavitational radiation therapy.

BACKGROUND AND SUMMARY OF THE INVENTION

Interstitial radiation therapy has been performed since the beginning of the 20th Century. Radium was developed by Madam Curie and Alexander Graham Bell proposed the use of radium in treating tumors. Subsequently, metal needles were developed in which a radium isotope was encapsulated for insertion in close proximity or into tumors. Where the tumor was deep seated, an operation was necessary to provide access to the tumor. Such therapy had serious problems and disadvantages. The high energy of the radium isotope requird a great deal of shielding and subjected the personnel to harmful exposure. In addition, the needles tended to break as they aged resulting in the release of the radioactive contents. Since the radium isotopes had a half-life of about 1600 years, they produced an extreme contamination hazard.

Thus, efforts have been made to develop new isotopes and delivery systems making brachytherapy safer and more convenient to use. New isotopes have lower energies requiring less shielding and shorter half-lives reducing the risk of contamination.

Permanent seeds of encapsulated radon-222 having an energy level of 0.78 MEV and a half-life of 33.83 days or of encapsulated gold-198 having an energy level of 0.42 MEV and a half-life of 2.7 days have been used. More recently small seeds of iridium-192 having an energy level of 0.30 MEV and a half-life of 74.2 days and iodine-125 having an energy level of 0.028 MEV and a half-life of 60 days have been developed. Such seeds are shown, for example, in U.S. Pat. Nos. 3,351,049 and 4,323,055.

Such iridium and iodine seeds are on the order of 4.5 mm in length and 0.8 mm in diameter and are implanted in the tumor or placed in the surface of the tumor. Both of these sources have lower energies than radium that allow for simple shielding and less radiation exposure to personnel. With seeds of iodine encapsulated in a material such as titanium, shielding is provided by the surrounding tissue and the seeds can be left in the patient permanently without the need for major precautions.

Developments in delivery systems have been made in the types of applicators for placing radioactive sources either on the surface, interspread throughout the tissues (interstitial) and intercavity that is surrounded by tumor (intercavitary). Interstitial placement of seed requires the placement of hollow metal needles inserted through the normal tissues and into the tumor. Then the seeds are there after inserted into the needles, while the needles are being retracted to deposit the seeds in the tumor. Such devices are shown in the U.S. Pat. No. 4,402,308. The most commonly used instruments are the Henschke and Mick devices.

The placement of seeds on the surface of the tumors, tumors that are deep within the body require plastic catheters to be sutured over the treated area and seeds placed in the catheters by insertion of nylon tubes carrying the seeds. Catheters and seeds are removed when the proper dose is delivered. A permanent surface implant can also be preformed using I-125 seeds initially placed by hand in a woven or braided absorbable carrier such as a braided suture. The carrier with the seeds laced therein is then secured in place to form a suitable implant. This technique is time consuming and may necessitate handling of the suture as well as having the same problems as to position and retention as the catheters. In order to minimize the radiation to personnel during handling and shipping, the suture with the seeds placed therein is shielded by placing it in a curved metallic tube. See European Patent Application Publication No. 0,064,860, published 17.11.82, Bulletin 82/46.

The last method being the intercavitary placement of radioactive seeds is the method that pertains particularly to this patent. Intracavitary brachytherapy provides the ability to place radioactive material within and around a tumor to give the advantage of a high local tumor dose with normal tissue sparring as compared with an external beam apparatus alone. Intracavitary brachytherapy of gynecological tumors, due to the accessability of the vaginal and uterine cavities, allow easy insertion of radioactive sources. Today intracavitary brachytherapy has considerably improved local control and survival when using radiotherapy. It is known at this time that when cervical carcinoma is locally extensive the combination of brachytherapy and external beam has doubled survival over radical surgery alone. Today the Fletcher-Suit intracavitary applicator is the most commonly used gynecological applicator. Its development incorporates features found most important for local tumor control and minimized complications. These factors include fixation of the radioactive source geometry in relation to the normal pelvic structures, and separating the normal structures adjacent to the applicator from the sources. The system consists of a tandem used to hold radioactive sources in the uterine cavity, thus allowing a radioactive material to be located close to the tumor's center. Two hollow cylinders are placed in the vaginal fornices that hold radioactive seeds within the center of each cylinder. These cylinders are stainless steel and are actually modifications of the hollowed corks used in the Manchester system. The cylinders are attached to handles, which allow stabilization of the tandem with respect to the pelvis. It is well recognized now that the tandem and the cylinders improve the dose distribution by spacing the adjacent normal tissues from the radioactive source surface. Due to the exponential drop in dose rate as a function of distance, one is able to decrease local necrosis due to high surface doses of adjacent tissue as compared to radiation given at depth. This has been elaborated on by Rottman, M. in a publication titled "Intercavitary Applicator in Relation to Complications of Pelvic Irradiation", published in the *International Journal of Radiology, Oncology, and Physics*, 4:951–956, 1978.

The present invention is described to allow radiation treatment to be delivered by intracavitary means to what was previously considered to be a inaccessible site.

An example of such a site includes the brain. At the time of craniotomy a cavity is formed when the tumor is removed from the brain. The craniotomy carries a significant morbidity, and possible mortality due to anesthetic risks as well as infections and hemorrhagic complications. Thus, eliminating the necessity of a second surgical procedure to remove a radioactive source and eliminating an incision that can act as a portal for bacteria would increase the applicability of using intracavitary brachytherapy. A permanent implant would allow for immediate closure of the surgical wound and remove the necessity of a second surgical procedure.

Prior efforts to treat tumors in the brain have been by insertion of catheters and radioactive sources into the tumor or by removing the tumor by surgical techniques. In each instance, it has been difficult to insure whether proper treatment has been made and that the entire tumor has been properly treated.

Accordingly, among the objectives of the present invention are to provide a delivery system which will deliver proper radiation in instances where the tumor has been surgically removed; which system will continue to treat the surface area of the brain without necrosis of normal tissue and which can be permanently left in the brain.

In accordance with the invention, a delivery system for intracavitational brachytherapy comprises a body of material which is absorbable in animal tissue and a plurality of radioactive seeds within the body and encapsulated in the body. In one form, the body is hollow within an exterior wall defining a separate central chamber such that the hollow body exterior wall structure will accommodate growth of body tissue such as brain tissue. In another form, the body comprises a hollow body having the seeds held in the center of the body that can be inserted in the cavity to be treated. In another form, a flat sheet is attached tangentially to the hollow exterior wall to facilitate placement over the brain.

DESCRIPTION OF THE DRAWINGS

FIG. 1 is an elevational view of an intracavitational brachytherapy device embodying the invention.

FIG. 2 is a part sectional view of the device shown in FIG. 1.

FIG. 3 is a sectional view taken along the line 3—3 in FIG. 1.

FIG. 4 is a view showing the device utilized in a cavity from which a tumor has been removed.

FIG. 5 is an elevational view of a further modified form of the device.

FIG. 6 is a sectional view taken along the line 6—6 in FIG. 5.

FIG. 7 is a plan view of the device shown in FIG. 5.

FIG. 8 is a longitudinal sectional view through a modified form of the device.

FIG. 9 is a perspective view of the device shown in FIG. 8.

DESCRIPTION

In accordance with the invention, the intracavitational radiation therapy device embodying the invention comprises a body of material which is absorbable in animal tissue in the form of a geometric shape generally conforming to the cavity which remains after a tumor has been removed. A plurality of radioactive sources, such as seeds, are encapsulated in the center of the body.

The body can be made of any of the natural or synthetic absorbable materials. Examples of natural absorbable materials are the polyester amides from glycolic or lactic acids such as the polymers and copolymers of glycolide and lactide, polydioxanone and the like. Such polymeric materials are more fully described in U.S. Pat. Nos. 3,565,869, 3,636,956, 4,052,988 and European Patent Application No. 30822. Specific examples of absorbable polymeric materials that may be used to produce the substantially nondeflecting members of the present invention are polymers made by ETHICON, Inc., Somerville, N.J., under the trademarks "VICRYL" and "PDS".

The absorbable material should preferably maintain its integrity for from 1 to 14 days. Preferably the material should be absorbed in living tissue in a period of time of from about 70 to 120 days. It is preferred that as little absorbable material as possible be used in the delivery systems of the present invention.

The seeds can be various types having low energy and low half-life such as iodine seeds, known as I-125 seeds, consisting of a welded titanium capsule containing iodine 125 absorbed on a silver rod. Iridium seeds, designated Ir-192 seeds, can also be used.

In the form shown in FIGS. 1–3, the body 10 comprises a hollow ovoid or sphere 11, defined by an exterior, thin wall, which has a central portion 12 defining a diametral cavity 13 receiving the seeds 14. The end of the cavity is closed by a plastic plug or closure 15 of absorbable material.

When a tumor is removed from a body such as the brain leaving a cavity, the body 10 with the seeds is placed in the cavity. The hollow defining wall 14 of the body has sufficient flexibility such that as the half life of the radioactive sources is exceeded and the body 10 becomes absorbed, the tissue of the brain normally moves inwardly as shown in FIG. 4.

The provision of the body with the hollow exterior sphere 11 and the central diametral portion 12 provides a lightweight delivery system which also minimizes the amount of absorbable material left in the brain.

In the form shown in FIGS. 5, 6 and 7, the body 20 is solid and includes a diametral cavity 21 receiving the seeds S, the ends of the cavity being closed by plugs 22.

In a typical example:

1. A crainotomy is performed for surgical debulking of the tumor.

2. A properly shaped body is selected (spherical or cylindrical) and diameter (0.5 to 3 cm) absorbable polymer ovoid for implant.

3. The radioactive sources, such as I-125 seeds, are inserted into the ovoid to deliver a dose of 3000 rads over one year (source life) at a distance of 2 cm from the ovoid surface.

The advantages of using absorbable material in implants includes the light weight and lack of tissue reaction. Light weight bodies are preferred and are achieved in the hollow form of FIGS. 1-3. The importance of this in the brain is immediately seen in that the tissues would not be able to support a heavy object without migration due to gravity. A heavy object implanted in the brain may cause discomfort.

The fact that the body 10,20 is absorbable has the advantage of eliminating itself as a nitious for bacterial contamination. This is of prime importance in treating brain tumors with its inability to tolerate infection.

The importance of decreasing the ratio of dose at the implant surface can be appreciated both theoretically and clinically. Dose rate decreases as the square of the distance. In malignant gliomas of the brain, 96% of the failures are due to local recurrence within two centimeters of the primary tumor. This is due to the local invasiveness of the primary tumor. After a debulking procedure, there will be a high concentration of microscopic disease around the surgical defect, presumed to be approximately 2 cm. This volume of tissue requires a boosting dose in the order to 6000 rads to 7000 rads as shown by previous experience in head and neck tumors as well as in brain tumors. Usually 4500 rads are given by large field and a boosting dose via the implant for an additional 3000 rads. Implanting a nude source of radioactive I-125 the surface dose will be 100,000 rads for a dose of 3000 rads at the surface. By implanting the source in a spherical or cylindrical container, the surface dose will be 5,000 rads for a 2 cm diameter ovoid. Then the ratio in surface dose by using the ovoid range from 6,000 to 5,000, which should significantly reduce the hazard of radiation necrosis.

The form of device shown in FIGS. 8 and 9 is similar to that shown in FIGS. 1-4 with the addition of a sheet of nonabsorbable plastic, such as nylon, fixed tangentially to the sphere 11 and the closure 15 provided so that it is in the end of the central portion 12a which is tangential to the sheet 16.

In use, the sphere is placed within the cavity remaining after the tumor is removed and the sheet 16 attached thereto is utilized for suturing to the brain as at 17.

In all the embodiments that are shown in FIGS. 1-8, the geometric shape is a closed geometric shape such that a closed curve is produced when an imaginary plane extends through the shape. The closed curve is principally defined at the periphery of the shape. The claims appended hereto utilize the term "closed geometric shape" in this fashion.

What is claimed is:

1. A delivery system for intracavitational brachytherapy comprising:
   a body of a material which is absorbable in animal tissue,
   said body having a completely closed geometrical shape conforming generally with a cavity which is to be treated after removal of a tumor,
   and a plurality of radioactive seeds that are nonabsorbable within the body, said body becoming flexible due to absorption as the half-life of the radioactive sources is exceeded and diminishing in size with said cavity.

2. The delivery system set forth in claim 1 wherein said body is hollow and includes an exterior wall and an internal chamber containing said radioactive seeds.

3. The delivery system set forth in claim 2 wherein said plurality of radioactive seeds have a predetermined half-life and said body has sufficient flexibility such that the closed geometric shape diminishes in size as the half-life of said radioactive seeds is exceeded.

4. The delivery system set forth in claim 2 wherein said body is spherical.

5. The delivery system set forth in any of claims 1-4 wherein said body includes a removable closure for providing loading of the seeds prior to use.

6. The delivery system set forth in any of claims 1-4 including a sheet of non-absorbable material attached to said body.

7. The delivery system set forth in claim 6 wherein said body includes a removable closure for providing loading of the seeds prior to use, said closure being generally in the plane of said sheet.

8. The delivery system set forth in claim 1 wherein said plurality of radioactive seeds are spaced from the periphery of said body a predetermined distance.

9. A delivery system for intracavitational brachytherapy comprising:
   a plurality of radioactive seeds, that are not absorbable in animal tissue, encapsulated by a body of material that is absorbable in animal tissue, said body having a first and a second part, said first part completely encapsulating and isolating said plurality of seeds from adjacent tissue defining a cavity of a tumor, said second part retaining said plurality of seeds in a predetermined, spaced apart, fixed relation with respect to the periphery of said first part, said body diminishing in size due to absorption as the half-life of the radioactive sources is exceeded and diminishing in size along with said cavity.

10. A delivery system as claimed in claim 9 wherein said first part includes a removable closure for loading said seeds prior to use.

* * * * *